United States Patent
Gilad et al.

(10) Patent No.: US 7,662,093 B2
(45) Date of Patent: Feb. 16, 2010

(54) REDUCED SIZE IMAGING DEVICE

(75) Inventors: Zvika Gilad, Haifa (IL); Gavriel J. Iddan, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 576 days.

(21) Appl. No.: 10/529,736

(22) PCT Filed: Sep. 30, 2003

(86) PCT No.: PCT/IL03/00785

§ 371 (c)(1),
(2), (4) Date: Mar. 30, 2005

(87) PCT Pub. No.: WO2004/028336

PCT Pub. Date: Apr. 8, 2004

(65) Prior Publication Data

US 2006/0004256 A1    Jan. 5, 2006

Related U.S. Application Data

(60) Provisional application No. 60/414,414, filed on Sep. 30, 2002.

(51) Int. Cl.
*A61B 1/00* (2006.01)
*A61B 1/05* (2006.01)
*A61B 1/06* (2006.01)
(52) U.S. Cl. .................. 600/160; 600/109; 600/130
(58) Field of Classification Search .......... 600/160, 600/109, 130, 302; 348/65, 76
See application file for complete search history.

(56) References Cited

U.S. PATENT DOCUMENTS

| | | | |
|---|---|---|---|
| 3,683,890 A | 8/1972 | Beal | |
| 3,971,362 A | 7/1976 | Pope et al. | |
| 4,178,735 A | 12/1979 | Jackson | |
| 4,239,040 A | 12/1980 | Hosoya et al. | |
| 4,262,632 A | 4/1981 | Hanton et al. | |
| 4,278,077 A | 7/1981 | Mizumoto | |
| 4,439,197 A | 3/1984 | Honda et al. | |
| 4,495,546 A * | 1/1985 | Nakamura et al. | 361/749 |
| 4,646,724 A | 3/1987 | Sato et al. | |
| 4,689,621 A | 8/1987 | Kleinberg | |
| 4,803,992 A | 2/1989 | Lemelson | |
| 4,819,620 A | 4/1989 | Okutsu | |
| 4,844,076 A | 7/1989 | Lesho et al. | |

(Continued)

FOREIGN PATENT DOCUMENTS

DE    2929429    2/1980

(Continued)

OTHER PUBLICATIONS

U.S. Appl. No. 09/807,892, filed Jun. 6, 2001, Meron et al.

(Continued)

*Primary Examiner*—John P Leubecker
(74) *Attorney, Agent, or Firm*—Pearl Cohen Zedek Latzer, LLP (57) ABSTRACT

A reduced diameter in vivo imaging device, such as a swallowable imaging capsule. The imaging device includes a first circuit board configured for accommodating at least an image sensor, and a second circuit board, which is in electrical communication with the first circuit board and which extends substantially perpendicularly from the bottom surface of the first circuit board.

25 Claims, 8 Drawing Sheets

U.S. PATENT DOCUMENTS

| | | | |
|---|---|---|---|
| 4,936,823 A | 6/1990 | Colvin et al. | |
| 4,940,997 A | 7/1990 | Hamlin et al. | |
| 5,021,888 A * | 6/1991 | Kondou et al. | 348/76 |
| 5,031,072 A * | 7/1991 | Malhi et al. | 361/706 |
| 5,042,486 A | 8/1991 | Pfeiler et al. | |
| 5,081,041 A | 1/1992 | Yafuso et al. | |
| 5,109,870 A | 5/1992 | Silny et al. | |
| 5,187,572 A | 2/1993 | Nakamura et al. | |
| 5,211,165 A | 5/1993 | Dumoulin et al. | |
| 5,220,198 A * | 6/1993 | Tsuji | 257/731 |
| 5,241,170 A | 8/1993 | Field, Jr. et al. | |
| 5,259,795 A * | 11/1993 | Yamada et al. | 439/751 |
| 5,267,033 A | 11/1993 | Hoshino | |
| 5,279,607 A | 1/1994 | Schentag et al. | |
| 5,330,427 A | 7/1994 | Weissenburger | |
| 5,368,027 A | 11/1994 | Lubbers et al. | |
| 5,381,784 A | 1/1995 | Adair | |
| 5,395,366 A | 3/1995 | D'Andrea et al. | |
| 5,398,670 A | 3/1995 | Ortiz et al. | |
| 5,429,132 A | 7/1995 | Guy et al. | |
| 5,479,935 A | 1/1996 | Essen-Moller | |
| 5,495,114 A | 2/1996 | Adair | |
| 5,545,924 A * | 8/1996 | Contolatis et al. | 257/724 |
| 5,549,109 A | 8/1996 | Samson et al. | |
| 5,558,640 A | 9/1996 | Pfeiler et al. | |
| 5,604,531 A | 2/1997 | Iddan et al. | |
| 5,629,839 A * | 5/1997 | Woychik | 361/803 |
| 5,697,384 A | 12/1997 | Miyawaki et al. | |
| 5,734,418 A | 3/1998 | Danna | |
| 5,754,313 A * | 5/1998 | Pelchy et al. | 358/473 |
| 5,780,834 A * | 7/1998 | Havens et al. | 235/462.1 |
| 5,800,350 A | 9/1998 | Coppelson et al. | |
| 5,812,187 A | 9/1998 | Watanabe | |
| 5,819,736 A | 10/1998 | Avny et al. | |
| 5,833,603 A | 11/1998 | Kovacs et al. | |
| 5,837,196 A | 11/1998 | Pinkel et al. | |
| 5,857,963 A * | 1/1999 | Pelchy et al. | 600/109 |
| 5,867,069 A * | 2/1999 | Kiser | 331/96 |
| 5,908,294 A | 6/1999 | Schick et al. | |
| 5,913,820 A | 6/1999 | Bladen et al. | |
| 5,929,901 A | 7/1999 | Adair et al. | |
| 5,986,693 A | 11/1999 | Adair et al. | |
| 5,993,378 A | 11/1999 | Lemelson | |
| 6,033,234 A * | 3/2000 | Wang et al. | 439/67 |
| 6,043,839 A | 3/2000 | Adair et al. | |
| 6,088,606 A | 7/2000 | Ignotz et al. | |
| 6,099,482 A | 8/2000 | Brune et al. | |
| 6,128,201 A * | 10/2000 | Brown et al. | 361/784 |
| 6,149,581 A | 11/2000 | Klingenstein | |
| 6,174,291 B1 | 1/2001 | McMahon | |
| 6,228,048 B1 | 5/2001 | Robbins | |
| 6,233,476 B1 | 5/2001 | Stormmer et al. | |
| 6,240,312 B1 | 5/2001 | Alfano et al. | |
| 6,285,897 B1 | 9/2001 | Kilcoyne et al. | |
| 6,324,418 B1 | 11/2001 | Crowley et al. | |
| 6,369,812 B1 | 4/2002 | Lyriboz et al. | |
| 6,371,927 B1 * | 4/2002 | Brune et al. | 600/549 |
| 6,395,562 B1 | 5/2002 | Hammock et al. | |
| 6,400,338 B1 * | 6/2002 | Mejia et al. | 343/873 |
| 6,449,006 B1 | 9/2002 | Shipp | |
| 6,475,145 B1 | 11/2002 | Baylor | |
| 6,488,694 B1 | 12/2002 | Lau et al. | |
| 6,496,384 B1 * | 12/2002 | Morales et al. | 361/784 |
| 6,533,722 B2 * | 3/2003 | Nakashima | 600/179 |
| 6,547,721 B1 * | 4/2003 | Higuma et al. | 600/133 |
| 6,632,175 B1 * | 10/2003 | Marshall | 600/309 |
| 6,692,430 B2 | 2/2004 | Adler | |
| 6,939,292 B2 * | 9/2005 | Mizuno | 600/118 |
| 7,118,531 B2 * | 10/2006 | Krill | 600/309 |
| 2001/0017649 A1 | 8/2001 | Yaron | |
| 2001/0025135 A1 | 9/2001 | Naito et al. | |
| 2001/0035902 A1 | 11/2001 | Iddan et al. | |
| 2001/0051766 A1 | 12/2001 | Gazdzinski | |
| 2002/0015952 A1 | 2/2002 | Anderson et al. | |
| 2002/0103417 A1 | 8/2002 | Gazdzinski | |
| 2002/0146368 A1 | 10/2002 | Meron et al. | |
| 2002/0158976 A1 | 10/2002 | Vni et al. | |
| 2002/0171669 A1 | 11/2002 | Meron et al. | |
| 2002/0173718 A1 | 11/2002 | Frisch et al. | |
| 2002/0177779 A1 | 11/2002 | Adler et al. | |
| 2002/0193664 A1 | 12/2002 | Ross et al. | |
| 2002/0198439 A1 | 12/2002 | Mizuno | |
| 2003/0018280 A1 | 1/2003 | Lewkowicz et al. | |
| 2003/0020810 A1 | 1/2003 | Takizawa et al. | |
| 2003/0023150 A1 | 1/2003 | Yokoi et al. | |
| 2003/0028078 A1 | 2/2003 | Glukhovsky | |
| 2003/0032863 A1 * | 2/2003 | Kazakevich | 600/173 |
| 2003/0043263 A1 | 3/2003 | Glukhovsky et al. | |
| 2003/0045790 A1 | 3/2003 | Lewkowicz et al. | |
| 2003/0077223 A1 | 4/2003 | Glukhovsky et al. | |
| 2003/0114742 A1 | 6/2003 | Lewkowicz et al. | |
| 2003/0117491 A1 | 6/2003 | Avni et al. | |
| 2003/0130562 A1 * | 7/2003 | Barbato et al. | 600/109 |
| 2003/0151661 A1 | 8/2003 | Davidson et al. | |
| 2003/0167000 A1 | 9/2003 | Mullick et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0195415 A1 | 10/2003 | Iddan | |
| 2003/0208107 A1 | 11/2003 | Refael | |
| 2003/0214579 A1 | 11/2003 | Iddan | |
| 2003/0214580 A1 | 11/2003 | Iddan | |
| 2003/0216622 A1 | 11/2003 | Meron et al. | |
| 2004/0027459 A1 | 2/2004 | Segawa et al. | |
| 2004/0027500 A1 | 2/2004 | Davidson et al. | |
| 2004/0171914 A1 * | 9/2004 | Avni | 600/160 |
| 2004/0254455 A1 | 12/2004 | Iddan | |
| 2004/0258328 A1 | 12/2004 | Adler | |
| 2005/0267328 A1 * | 12/2005 | Blumzvig et al. | 600/109 |
| 2006/0241407 A1 * | 10/2006 | Scarantino et al. | 600/427 |

FOREIGN PATENT DOCUMENTS

| | | |
|---|---|---|
| DE | 34 40 177 | 6/1986 |
| FR | 2 688 997 | 10/1993 |
| IL | 126727 | 10/1998 |
| IL | 143258 | 5/2001 |
| IL | 143259 | 5/2001 |
| JP | 4109927 | 4/1992 |
| JP | 4144533 | 5/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2000342524 | 12/2000 |
| JP | 2000342525 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |

| | | |
|---|---|---|
| JP | 2002010990 | 1/2002 |
| WO | 98-11816 | 3/1998 |
| WO | 99/32028 | 7/1999 |
| WO | 01-08548 | 2/2001 |
| WO | 01-10291 | 2/2001 |
| WO | 01/50941 | 7/2001 |
| WO | 01-65995 | 9/2001 |
| WO | 01/69212 | 9/2001 |
| WO | 02-054932 | 7/2002 |
| WO | 02/55126 | 7/2002 |
| WO | 02/55984 | 7/2002 |
| WO | 02-67593 | 8/2002 |
| WO | 02-080376 | 10/2002 |
| WO | 02/094337 | 11/2002 |
| WO | 02-102224 | 12/2002 |
| WO | 03/003706 | 1/2003 |
| WO | 03/011103 | 2/2003 |
| WO | 2004-028335 | 4/2004 |
| WO | 2004/035106 | 4/2004 |
| WO | WO 2004/028336 | 4/2004 |
| WO | 2004-088448 | 10/2004 |

OTHER PUBLICATIONS

U.S. Appl. No. 10/166,025, filed Jun. 11, 2002, Lewkowicz et al.
U.S. Appl. No. 10/200,548, filed Jul. 23, 2002, Glukhovsky et al.
U.S. Appl. No. 10/213,345, filed Aug. 7, 2002, Glukhovsky.
U.S. Appl. No. 10/482,218, filed Dec. 29, 2003, Glukhovsky et al.
U.S. Appl. No. 10/724,109, filed Dec. 1, 2003, Glukhovsky et al.
U.S. Appl. No. 60/297,761, filed Jun. 14, 2001, Lewkowicz et al.
U.S. Appl. No. 60/301,141, filed Jun. 28, 2001, Glukhovsky et al.
U.S. Appl. No. 60/309,181, filed Aug. 2, 2001, Glukhovsky.
BBC News Online—Pill camera to 'broadcast from the gut', Feb. 21, 2000, www.news.bbc.co.uk, printed Oct. 22, 2002.
Bio-Medical Telemetry: Sensing and Transmitting Biological Information from Animals and Man, R. Stuart Mackay, John Wiley and Sons, New York, 1970, pp. 244-245.
Deep Subsurface Imaging in Tissues Using Spectral and Polarization Filtering. S G Demos Jul. 3, 2000 vol. 7, No. 1 Optics Express, pp. 23-28.
Evaluation of the Heidelberg pH Capsule: Method of Tubeless Gastric Analysis, Yarbrough, III et al., The American Journal of Surgery, vol. 117, Feb. 1969, pp. 185-192.
Heidelberger Kapsel—"ein Kleinstsender fur die pH-Messung im Magen", Lange, et al., Telefunken-Zeitung, Jg 36 (1963) Heft 5, pp. 265-270.
"In Pursuit of the Ultimate Lamp", Craford et al., Scientific American, Feb. 2001.
International Search Report for PCT/IL99/0554 dated Apr. 4, 2000.
International Search Report of PCT/IL02/00391, dated May 19, 2003.
International Search Report of International Application No. PCT/IL02/00526, dated Mar. 7, 2003.
Katgraber F, Glenewinkel F, Fischler S, Int J. Legal Med 1998; 111(3) 154-6.
"Manual of Photogrammetry", Thompson (Ed.), Third Edition, vol. Two, Copyright 1944, 1952, 1966 by the American Society of Photogrammetry.
www.jason.net/tinycam.htm, © 2001, printed Dec. 19, 2001.
www.middleeasthealthmag.com/article2.htm—Review proves the value of computers, © 2001, printed Nov. 29, 2001.
www.pedinc.com Personal electronic devices, © 1997.
"New Smart Plastic has Good Memory"—Turke, European Medical Device Manufacturer, devicelink.com, date unknown.
"Robots for the Future"—Shin-ichi, et al. http://jin.jcic.or.jp/nipponaia13/sp05 html. printed Nov. 29, 2001.
Supplementary Partial European Search Report, Mar. 19, 2004.
"The Heidelburg pH Capsule System Telemetric Fasting Gastric Analysis", Heidelburg International. Incorporated, date unknown.
"The Radio Pill", Rowlands, et al., British Communications and Electronics, Aug. 1960, pp. 598-601.
Video Camera to "Take"—RF System Lab, Dec. 25, 2001.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
"Wellesley Company Sends Body Montiors into Space"—Crum, Boston Business Journal, 1998.
"Wireless Transmission of a Color Television Moving Image from the Stomach using a Miniature CCD Camera, Light Source and Microwave Transmitter." Swain CP, Gong F, Mills TN. Gastrointest Endosc 1997;45:AB40, vol. 45, No. 4, 1997.
www.rfnorkia.com—NORIKA3, printed on Jan. 1, 2002.

* cited by examiner

REDUCED SIZE IMAGING DEVICE

CROSS-REFERENCE TO RELATED APPLICATIONS

This application is a National Phase Application of PCT International Application PCT/IL2003/000785, filed Sep. 30, 2003, which claims priority of U.S. Provisional Application 60/414,414, filed Sep. 30, 2002 both of which are being incorporated here in their entirety.

FIELD OF THE INVENTION

The present invention relates to imaging devices, and particularly to imaging devices including configurations allowing for reduced area, size, length or reduced diameter or cross-sectional area.

BACKGROUND OF THE INVENTION

Remote imaging and other sensing devices are used in numerous industrial and medical applications. Many of these applications call for the imaging of areas that can be reached only by way of narrow points of access. An example of such an application is in vivo imaging wherein an imaging device is inserted into a body lumen to image areas within the body.

Several factors have so far limited the extent to which the diameter or other dimensions of an imaging device can be reduced. A first factor is the diameter of the circuitry connected to the imaging sensor portion of the imaging device. This circuitry, generally in the form of an integrated circuit on a chip such as a silicon chip, may processes image signals generated by an imaging sensor. The circuit that processes the signals generated by the imaging sensor is generally referred to as the processing chip although such circuitry and such "processing chip" need not be on or associated with a traditional "chip". The diameter of the processing chip may be a limitation to possible reductions in the diameter, length or size in general of the imaging device.

A second factor that has limited the reduction in the size of imaging devices is the cumulative widths of the several components of the imaging device that in some configurations are situated on the plane of the imaging device which faces the surface to be imaged. These items have generally included, for example, at least the imaging sensor, which typically sits behind an optical lens, and at least one illumination source for illuminating the surface to be imaged. The placement of both of these components on the same plane has limited the possibility of reducing the diameter of such plane and hence the diameter of the imaging device.

The size of available imaging devices relative to the small openings of many body lumens or relative to body lumens of small diameter, such as in children, may be limiting. A reduced size imaging device may provide greater access to body lumens with narrow or restricted points of access. Furthermore, there may be a need to use space within imaging devices in a more efficient manner. There is a need for an imaging device with a reduced size such that the imaging device can be, for example, inserted or pass through very narrow points of access.

SUMMARY OF THE INVENTION

Some embodiments of the present invention may, for example, enable a reduced diameter, reduced length, or reduced size imaging or other sensing device. According to one embodiment, a processing chip or a board, circuit board, or holder holding such a chip, is aligned substantially perpendicular to the plane of an imaging sensor. The thickness of the processing chip can be small, such that as so aligned, the profile area of the processing chip does not constrain reductions in the diameter of the imaging device. The physical and electrical connection between the imaging sensor and the processing chip may be made by way of, for example, a printed circuit board (PCB), to which both the imaging sensor and the processing chip are connected. In an embodiment of the present invention, the imaging sensor is connected to the side edge of the PCB such that the PCB may also be situated substantially perpendicular to and behind the imaging sensor. The electrical connections that carry power from the PCB to the imaging sensor and that carry image signals from the imaging sensor to the PCB may be made for example by way of leads ending at the side edge of the PCB to which the imaging sensor is attached. The processing chip may then be attached to the PCB in parallel to the plane of the PCB, such plane typically being substantially perpendicular to the imaging sensor. The arrangement of the PCB and the processing chip substantially perpendicular to the imaging sensor allows a reduction in the diameter of the imaging device where reductions in such diameter may theretofore have been limited by the width of the PCB and the processing chip.

According to another embodiment, at least one light source, typically in the form of one or more light emitting diodes (LEDs), although other suitable light sources may be used, may be situated behind and substantially perpendicular to the plane of an imaging sensor. The light produced by the light source may be emitted for example parallel to the plane of the imaging sensor and can then be refracted or reflected by a light deflecting element, such as a prism or mirror, which is attached or otherwise held in place in the path of the light emitted by the light source. The refraction or path-alteration of the light deflecting element directs the light emitted by the light source towards the plane of the imaging sensor so that the light exits the imaging device substantially perpendicular to such plane. By situating the at least one light source behind and substantially perpendicular to the imaging sensor, it may be possible to reduce the diameter of the imaging device.

The device and system according to some embodiments of the present invention also may permit a reduction in the number of separate electrical connections that need be made between the various components of an imaging device and between the circuits to which such components are attached. In an embodiment of the present invention, any of the light sources and the processing chip may be attached directly to the PCB that may be situated substantially perpendicular to the imaging sensor. This PCB may be the same PCB to which the imaging sensor is attached. The connection of the light sources or the processing chip to the PCB may be by way of for example pins or other suitable connections that may provide either or both of a physical and electrical connection to the circuit. Similarly, such PCB may include a niche into which may be inserted and held one or more batteries or other power supply sources, such as rechargeable devices, which may be held in direct contact with the PCB. Such power sources may be held in parallel or perpendicular to the plain of the PCB. Such direct contact may provide either or both of a physical and electrical connection between such power supply and the PCB.

There is thus provided, according to an embodiment of the invention an in vivo imaging device, such as a swallowable imaging capsule. According to one embodiment the imaging device includes a first circuit board includes, or is configured for accommodating or having disposed thereon, at least an image sensor, and a second circuit board, which is in electrical communication with the first circuit board and which extends at an angle of between about 0° to about 180° from the bottom surface of the first circuit board. The first circuit board may be perpendicular to or substantially perpendicular to the first circuit board. The second circuit board may, for example, have disposed thereon a processing chip.

According to another embodiment of the invention there is provided a circuit board configured for being in electrical communication with another circuit board and extending substantially perpendicularly to the other circuit board.

Also provided, according to other embodiments of the invention is an image sensor which is configured for being in electrical communication with a circuit board, the circuit board extending substantially perpendicularly to the image sensor.

According to another embodiment there is provided, in an in vivo imaging device, a single circuit board that is configured for accommodating an image sensor and at least one illumination source.

According to yet another embodiment there is provided a circuit board which has a transmitter and a transmitter antenna, where the antenna is embedded into the circuit board.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

Figure 1A:
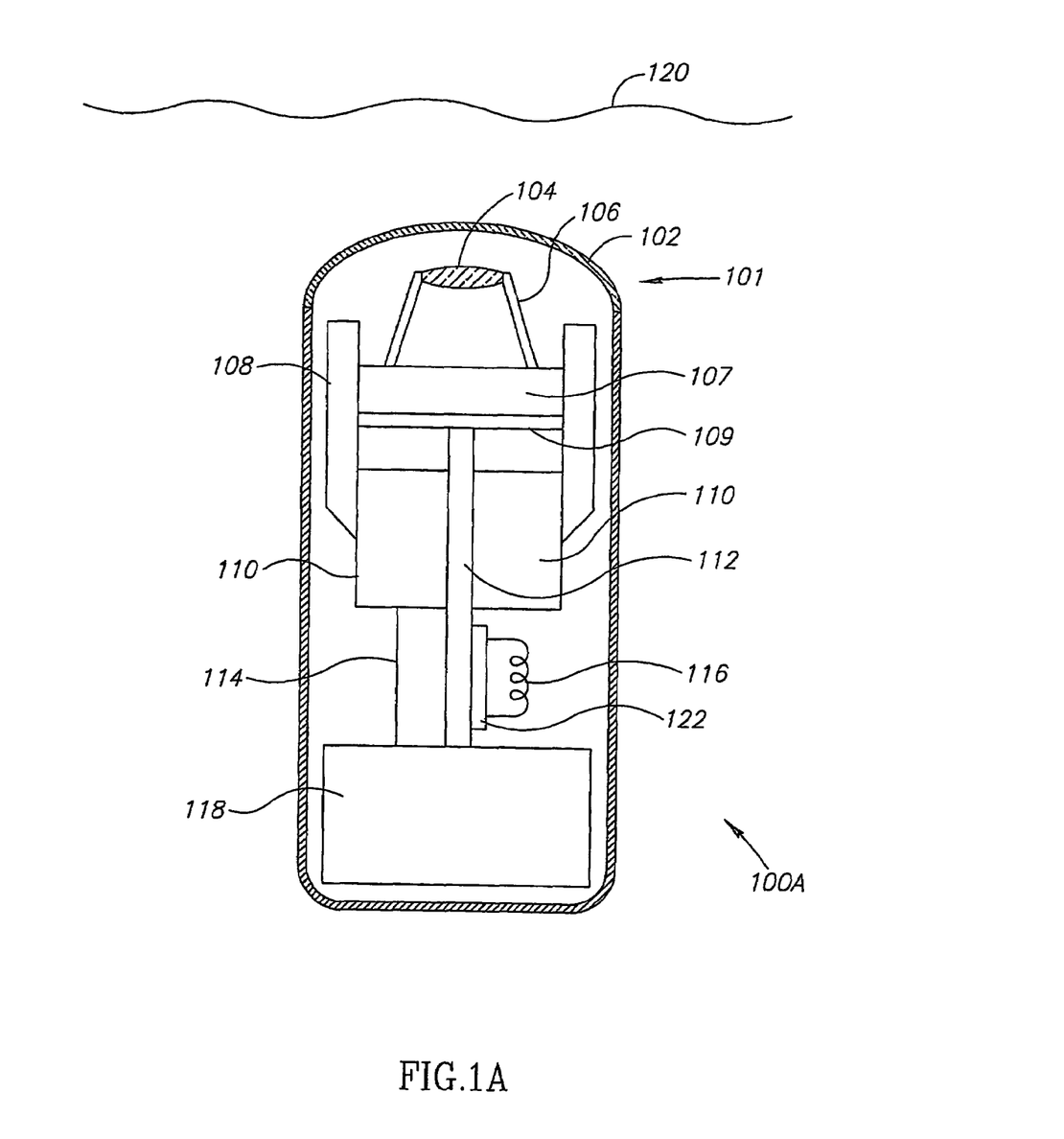
FIG. 1A is a simplified illustration of a reduced diameter imaging device wherein the processing chip, the circuit board and the light source are situated behind and substantially perpendicular to the plane of the imaging sensor, in accordance with an embodiment of the present invention.

Reference is made to FIG. 1A which shows a simplified illustration of a reduced size, length or size imaging device wherein a processing chip, a circuit board, such as a PCB, and the light source are situated behind and substantially perpendicular to the plane of the imaging sensor, in accordance with an embodiment of the present invention. The imaging device 100A may include an optical head 101, an imaging sensor 107, which is typically physically, electrically and/or electronically connected to an imaging sensor circuit board 109, a processing chip 114 that may, for example, processes the signals generated by imaging sensor 107, a circuit board 112 that connects imaging sensor circuit board 109 to processing chip 114 and possibly to certain other components of the imaging device 100A, one or more light sources 110 (e.g., light emitting diodes (LEDs) or other suitable sources) to illuminate the area to be imaged 120, one or more prisms 108 or other refracting or reflecting elements to, for example, refract or alter the path of the light produced by one or more light sources 110 and a power source which may for example include one or more batteries 118. Batteries 118 may be connected by wires (not shown) or other connections to the circuit board 112. The imaging device may also include, for example, a transmitter 122 to transmit the signals processed by processing chip 114 and an antenna 116 to be used in such transmission. Typically, transmitter 122 sends signals to an external receiver (not shown), which may receive and process such signals. In alternate embodiments, other components and arrangement of components may be used. For example, transmitter 122 need not be used. According to some embodiments processing chip 114 and transmitter 122 may be integrated on the same chip.

The imaging device 100A is typically autonomous, including a power source or power source receiving device and a transmitter for wirelessly transmitting data, but need not be. For example, a wired device, exchanging data and/or power with an external system via wires, may be used.

While various benefits such as size, length or size are discussed as resulting from the various embodiments discussed herein, other benefits may be realized. For example, more components may be included in a device where space is saved.

In one embodiment, circuit board 112 may include, or may be configured, for example, for holding or accommodating, components such as a processing chip 114, light source(s) 110, transmitter 122, or other suitable components. Circuit board 109 may include or may be configured, for example, for holding or accommodating an imaging sensor 107 or other components. In alternate embodiments, the various arrangements of components may be altered. For example, light sources may be included on the same board or holder as an imager.

In certain embodiments, a circuit board may include a switch. According to one embodiment the switch is a magnetic switch, such as a micro-electro-mechanical system (MEMS) switch. The switch may be configured to control at least one electrical component of, for example, an imaging device. The switch may be disposed between portions of the electrical circuitry of the device 100A, such that when the switch is open, some or all components of device 100A are powered off or on, or are operative or inoperative. A magnetic switch may be, for example, constructed of a suitable magnet or materials responsive to magnetic forces such that it may be moved and operated upon exposure of the device 100A to a magnetic field. Alternately, other suitable control circuits may be used.

Embodiments of the imaging device may include components and operate similarly to embodiments described in U.S. Pat. No. 5,604,531 to Iddan, et al. and/or WO 01/65995, both assigned to the common assignee of the present application and hereby incorporated by reference; however, embodiments of the present invention may be used with other imaging systems or other arrangements of components. Further, a receiving and display system as disclosed in embodiments described in U.S. Pat. No. 5,604,531 to Iddan, et al. and/or WO 01/65995 may be used with or included in embodiments of the present invention, although other suitable receiving and display systems may be used. Typically, the imaging device 100A is a capsule or capsule shaped device inserted into a body lumen such as, for example, the gastrointestinal tract, which transmits or otherwise sends images to an external receiver or recorder. For example, the device may be ingested. In alternate embodiments, the imaging device need not be a capsule. For example, the imaging device may be the tip of a medical device, such as, an endoscope, needle, catheter, stent etc.

The optical head 101 may include one or more optical elements, such as one or more lenses 104 and a lens holder 106. One or more suitable optical elements may be used for focusing images onto imaging sensor 107. The optical head 101 may be part of, attached to, mounted on or otherwise disposed adjacent to the imaging sensor 107. The optical head 101 may be placed behind an optical window or dome 102 to, for example, isolate its electric components from liquids found in a body, which may interfere with the operation of such components. The optical head 101 may be manufactured as a single assembly or may include separate assemblies that are connected in the imaging device. In alternate embodiments, the optical head need not be used, and other arrangements for focusing the image may be used.

The imaging sensor 107 may be, for example, a solid state imaging sensor, such as charged coupled devices (CCDs) and complementary metal oxide semiconductors (CMOS). The imaging sensor 107 can be, for example, 3 mm sq with an active area of about 1.8 square mm, with dimensions of about 0.8 mm in width. Other suitable dimensions may be used.

In a typical embodiment of the present invention, circuit board 112 lies at an angle from 0° to 180° to the plane of the imaging sensor, or from the plane of a circuit board or other holder holding or including the imaging sensor (e.g., circuit board 109). According to one embodiment the circuit board 112 is substantially perpendicular to the plane of imaging sensor 107 and imaging sensor circuit board 109. Circuit board 112 may include, for example, a PCB or other device for electrical and/or physical connection by which imaging sensor 107 and imaging sensor circuit board 109 can be held in place, by which power can be supplied to the image sensor 107 and by which signals can be conducted from the imaging sensor 107 to the processing chip 114 or other components. Alternatively, circuit board 112 can be used to transmit signals to the processing chip 114, while another mechanism is used to hold the imaging sensor 107 in place. Processing chip 114 may be attached to circuit board 112 such that it lies in parallel to circuit board 112 and perpendicular to the plane of imaging sensor 107 and imaging sensor circuit board 109. If circuit board 112 is a PCB, then processing chip 114 may, for example, be attached to such PCB by way of pins as are know in the art. Typically, processing chip 114 contains circuitry for processing image signals. According to some embodiments the device 100A may contain other in vivo sensors (such as, for example, pH sensors, temperature sensors, pressure sensors etc.) and the processing chip may contain circuitry for processing signals other than image signals.

Imaging sensor 107 may generate electronic signals such as image signals. Image signals may be transmitted by way of imaging sensor circuit board 109 through circuit board 112 to processor chip 114. Processor chip 114 may carry out processing or conditioning of the image signal, for example so that it may be viewed on a display system such as on a monitor, or for other reasons. An example of a processor chip that may be used in embodiments of the present invention is an ASIC (application specific integrated circuit). According to one embodiment the ASIC may have transmitting capabilities, for example, operating on a minimum shift keying (MSK) modulation system to effect transmitting of digital signals through an antenna on radio frequencies to a receiving system. The ASIC may also control the illumination and imaging sensor 107, for example as described in embodiments of the above mentioned WO 01/65995. In alternate embodiments, other signals and other electronic and processing components may be used. For example, a processor chip need not be included, or need not be mounted on the circuit board 112. Similarly, an imaging sensor circuit board 109 need not be used.

According to one embodiment device 100A is capsule shaped. In other embodiments of the present invention, the device may be constructed in other shapes such, for example, as a sphere, circular cylinder, an elliptical cylinder, a rectangle, a trapezoid or other suitable shapes.

Figure 1B:
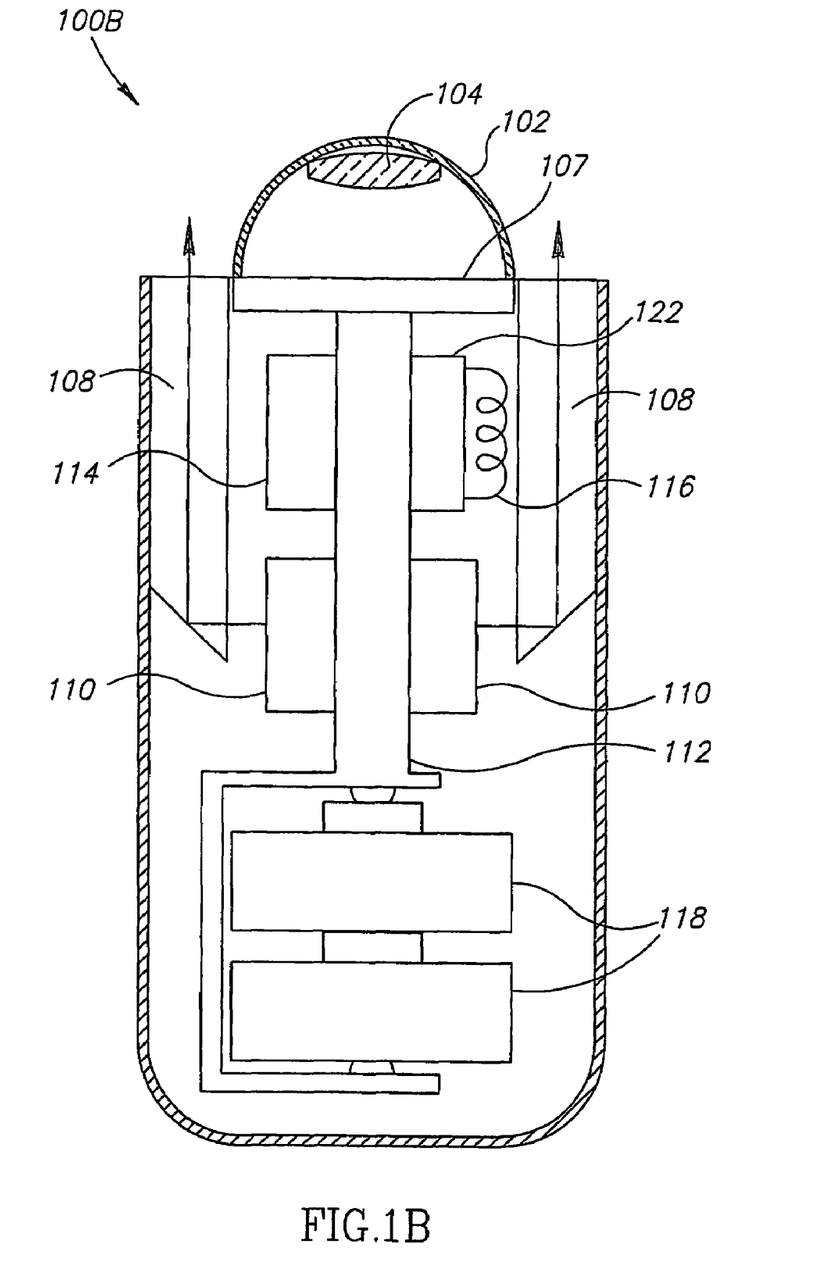
FIG. 1B is an illustration of an imaging device in accordance with another embodiment of the present invention.

FIG. 1B is an illustration of an alternative placement of certain components of imaging device 100B in accordance with an embodiment of the present invention. As is depicted in such illustration, processing chip 114 and transmitter 122 may be placed proximate to the location of imaging sensor 107, whereas light source 110 may be located more remotely from the imaging sensor 107. FIG. 1B likewise depicts an alternative embodiment of the present invention wherein one or more of prisms 108 are located outside of the coverage of optical window or dome 102. Such location of prisms 108 outside of the coverage of optical window or dome 102 may, for example, reduce the amount of back scatter light from the optical window or dome 102, although such a result is not required. Other configurations of one or more of prisms 108 or other light guides or light bending devices placed either inside or outside of the coverage of optical window or dome 102 are possible.

Figure 1C:
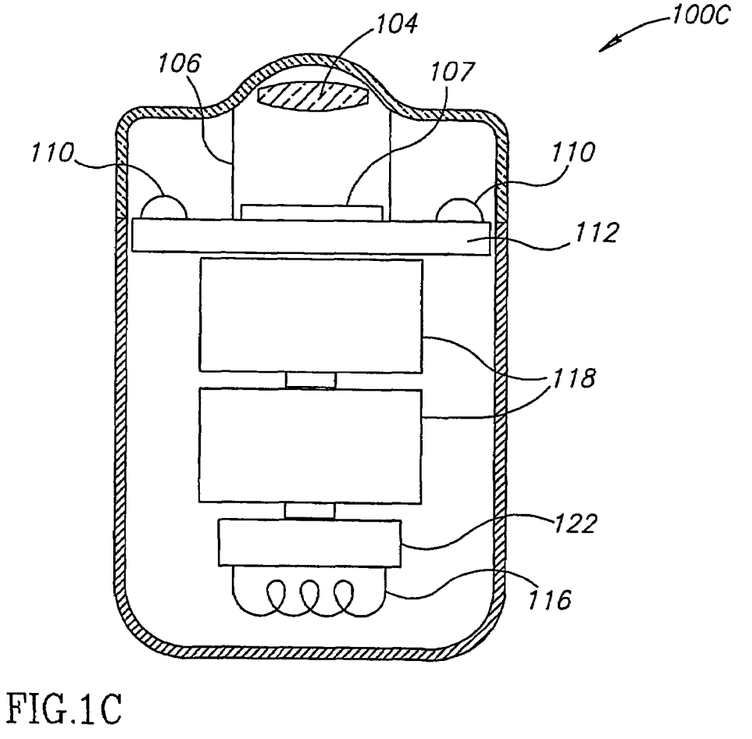
FIG. 1C is an illustration of an imaging device in accordance with yet another embodiment of the present invention.

FIG. 1C is an illustration of an alternative placement of certain components of imaging device 100C in accordance with another embodiment of the present invention. According to this embodiment illumination sources, such as Light sources 110 may be situated on the same circuit board 112 as the imaging sensor 107. Such placement may, for example, eliminate the need for imaging sensor circuit board 109, although such results are not required. Lens holder 106 may include, for example, opaque material or otherwise be constructed to ensure that light directly emitted from Light sources 110 is not incident on imaging sensor 107. A processing chip (not shown) may also be integrated on circuit board 112. Similar numerals to those in the figures described above have been assigned to like elements.

Figure 2A:
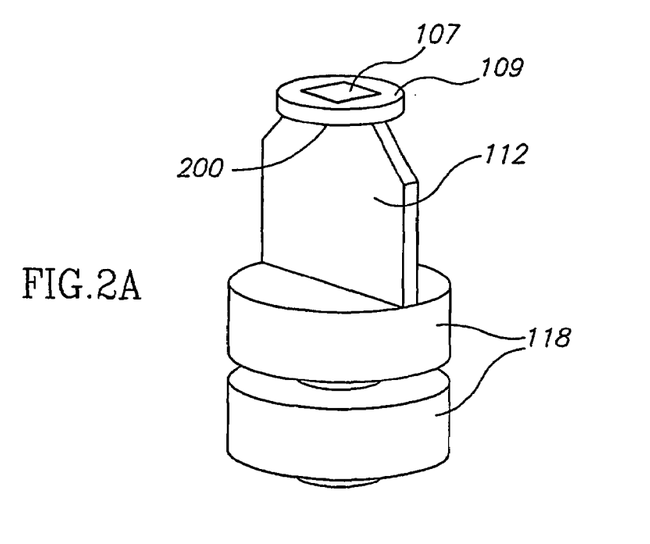
FIGS. 2A-2C are simplified illustrations of a connection of an imaging sensor onto a circuit board, in accordance with embodiments of the present invention.
Figures 2B, 2C:
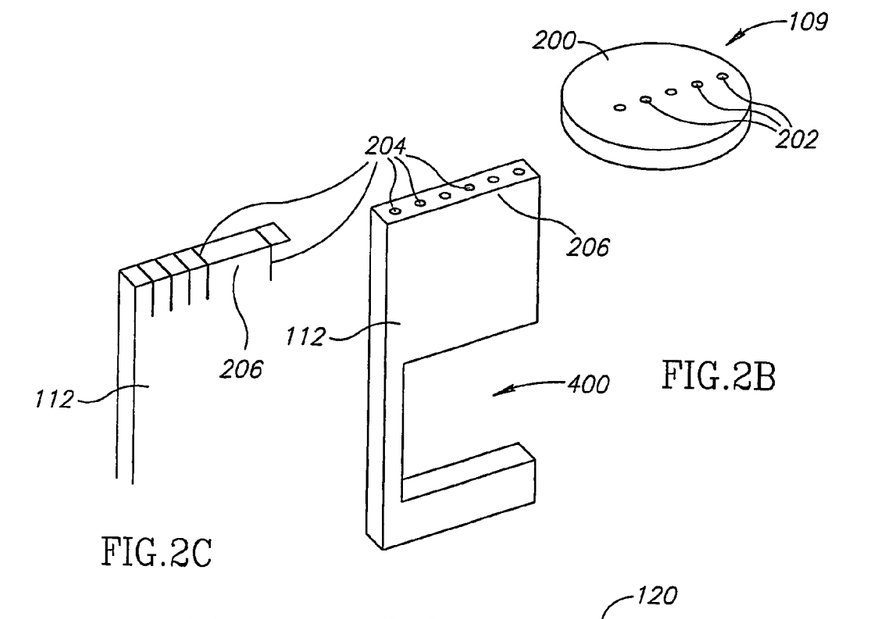

Reference is made to FIGS. 2A-2C which schematically illustrate a substantially connection of an imaging sensor and a circuit board with another circuit board in accordance with an embodiment of the present invention. The connection is typically perpendicular but other suitable angles may be used. In a typical embodiment, imaging sensor 107 rests on and is electrically connected to imaging sensor circuit board 109 by way of, for example, pins or other methods known in the art. The back surface 200 of imaging sensor circuit board 109, being the surface away from imaging sensor 107, may be fitted, for example, with at least one recess, such as socket or slot(s) 202 into which the side edge 206 of circuit board 112, or leads, connectors or tabs extending from circuit board 112, may be inserted and held. Slot(s) 202 may, for example, provide a secure physical connection between the back surface 200 of imaging sensor circuit board 109 and the side edge 206 of circuit board 112. Circuit board 112, as shown in FIG. 2B, may include leads 204 which are typically embedded in circuit board 112 providing an electrical connection between circuit board 112 and imaging sensor circuit board 109. Circuit board 112, shown in FIG. 2C may include leads 204 or other connectors ending at the side edge 206 of circuit board 112, typically in the outermost layer of the circuit board, providing an electrical connection between circuit board 112 and imaging sensor circuit board 109. Other arrangements of connecting circuit board 112 and image sensor circuit board 109, or providing electrical connections therebetween, or of holding image sensor 107 in place may also be used. For example, the back surface 200 may include clasps that may clasp onto the side edge 206 of circuit board 112. According to one embodiment circuit board 112 includes a recess or niche 400 which may be used to accommodate elements of the device, such as one or more batteries or other power sources, a battery pack or a suitable rechargeable power supply.

Figure 3:
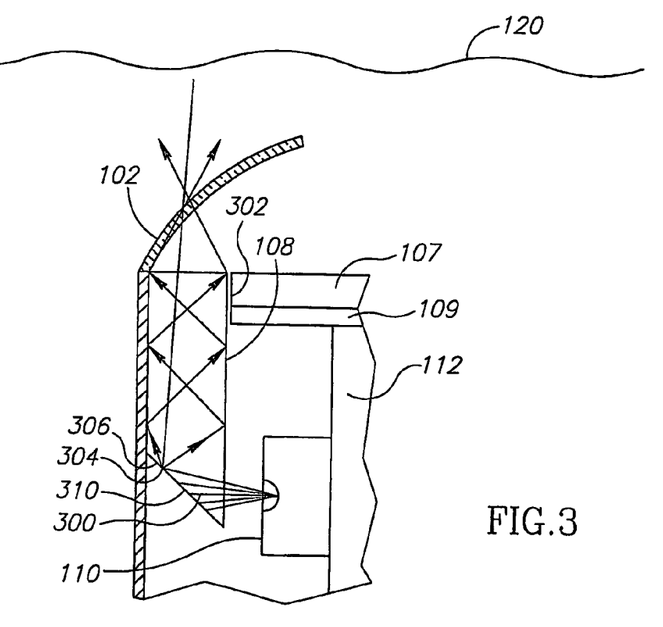
FIG. 3 is a simplified illustration of a light source situated behind and substantially perpendicular to the imaging sensor, and to which is attached a prism that alters the path of the light emitted by the light source, in accordance with an embodiment of the present invention.

Reference is made to FIG. 3 which is a simplified illustration of a light source assembly, typically situated behind and substantially perpendicular to an imaging sensor, and to which is attached a light guide or prism that may alter the path of the light emitted by the light source(s), in accordance with an embodiment of the present invention. The light source assembly may, for example, be used in embodiments of the device described herein, such as device 100A or other devices described herein. Light source 110 can be, for example, one or more light emitting diodes (LEDs) or other suitable sources of light. All or part of the light 300 produced by light source 110 may, for example, be emitted substantially perpendicular to the plane of circuit board 112 and substantially parallel to the plane of imaging sensor 107. Prism 108 may be affixed in the path of light 300. The angled edge 306 of prism 108 can be, for example, coated with silver or a similar reflective coating 310 to reflect light 300. Angled edge 306 of prism 108 is typically set at an angle of approximately 45 degrees relative to the surface of light source 110 and the point 304 thereon from which light 300 is emitted, although other suitable angles may be used. As light 300 is emitted from light source 110, it may be, for example, refracted by the prism 108 and/or reflected by the reflective coating 310 on angled edge 306 such that light 300 passes towards and through the optical dome 102 to illuminate the surface to be imaged 120. A light shield in the form of, for example, a reflective coating may also be added to other external surfaces of prism 108 to further direct light 300 towards the surface to be imaged 120. Light shield 302 may also, for example, prevent light 300 from reaching the imaging sensor 107 directly from prism 108. Prism 108 may be glued or otherwise attached to light source 110 or may be held in place by optical window or dome 102 or by other methods, for example mechanical methods. Other light redirecting devices may be used instead of a prism, such as a mirror or a fiber optic light guide.

Figure 4:
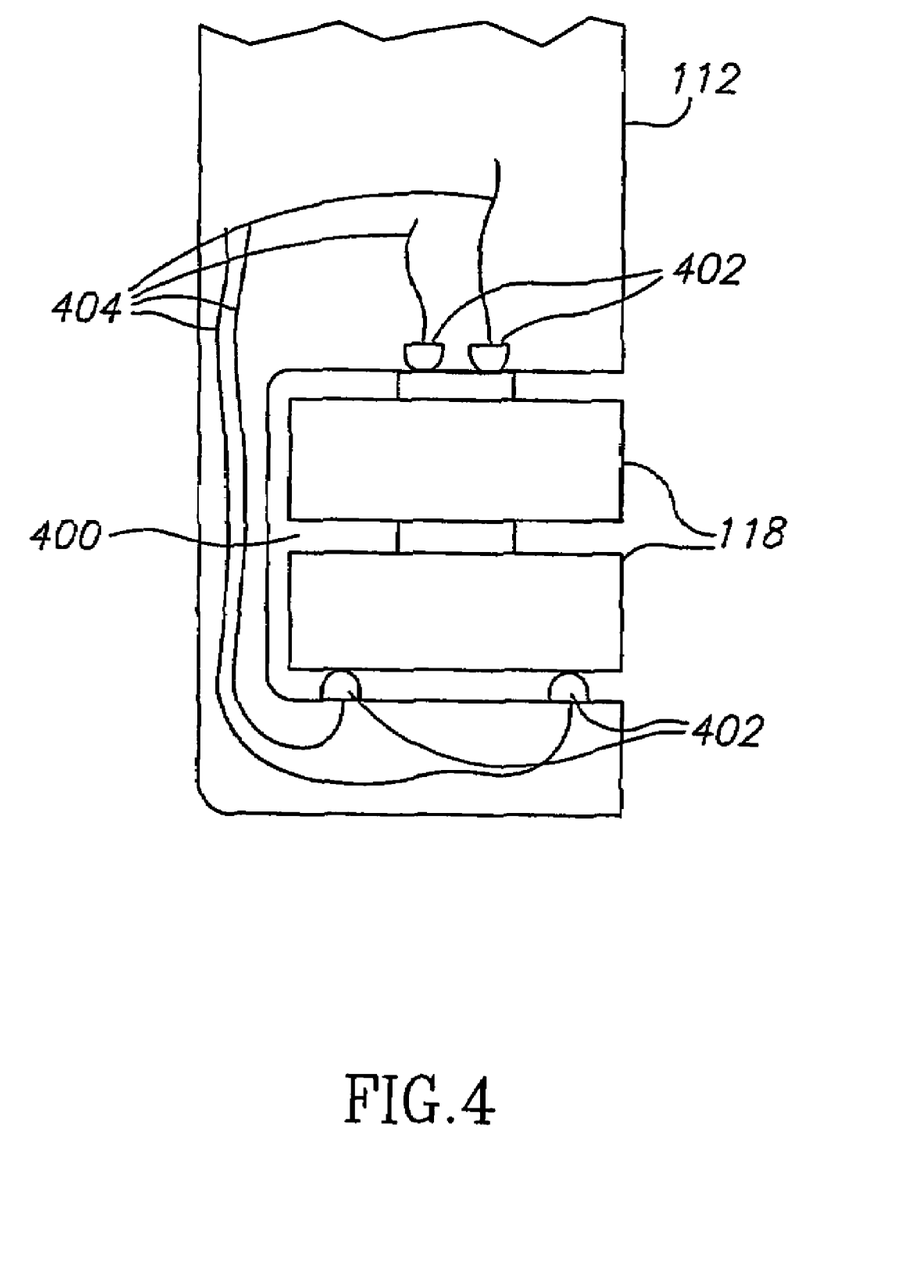
FIG. 4 is a simplified illustration of a circuit board, which includes a niche or other area into which may be inserted and held one or more batteries or other power source in accordance with an embodiment of the present invention.

Reference is made to FIG. 4, which is a simplified illustration of a circuit board in the form of a PCB. The circuit board 112 may, for example, be used in embodiments of the device described herein, such as device 100A or other devices described herein. The circuit board 112, according to an embodiment of the invention, is configured for containing or holding a power source, such as one or more batteries or a battery pack. For example, circuit board 112 includes an inset, cutout or niche 400 into which may be inserted and held one or more batteries 118 or other power source(s), which may be held in physical and electrical contact with the circuit board 112. Circuit board 112 may be, for example, a PCB, but other suitable structures may be used. Niche 400 may be constructed with, for example, one or more protrusions 402 to hold the one or more batteries 118 in place and to maintain electrical contact between circuit board 112 and the one or more batteries 118. Other methods of maintaining physical and electrical contact may also be used. Leads 404, which may for example be placed on circuit board 112, may conduct power from the one or more batteries 118 to the other components of the device. Batteries 118 may rest in parallel to or perpendicular with the plain of circuit board 112, or at another suitable angle therewith. Placement of one or more batteries 118 in direct electrical contact with circuit board 112 may reduce the number of electrical connections that are made between circuit board 112 and other components that are included in a device.

In various embodiments of the present invention, the circuit arrangement according to various embodiments described herein may be used without the illumination arrangement according to various embodiments described herein, and vice versa. Similarly, each of such arrangements may be used in conjunction with or without the arrangement described above for holding one or more power source within the niche 400. Likewise, the position of various components of the imaging device 100 such as the processing chip 114, transmitter 122, antenna 116, and power source, such as, for example, batteries 118 can be varied relative to each other and their location on circuit board 112.

Figure 5A:
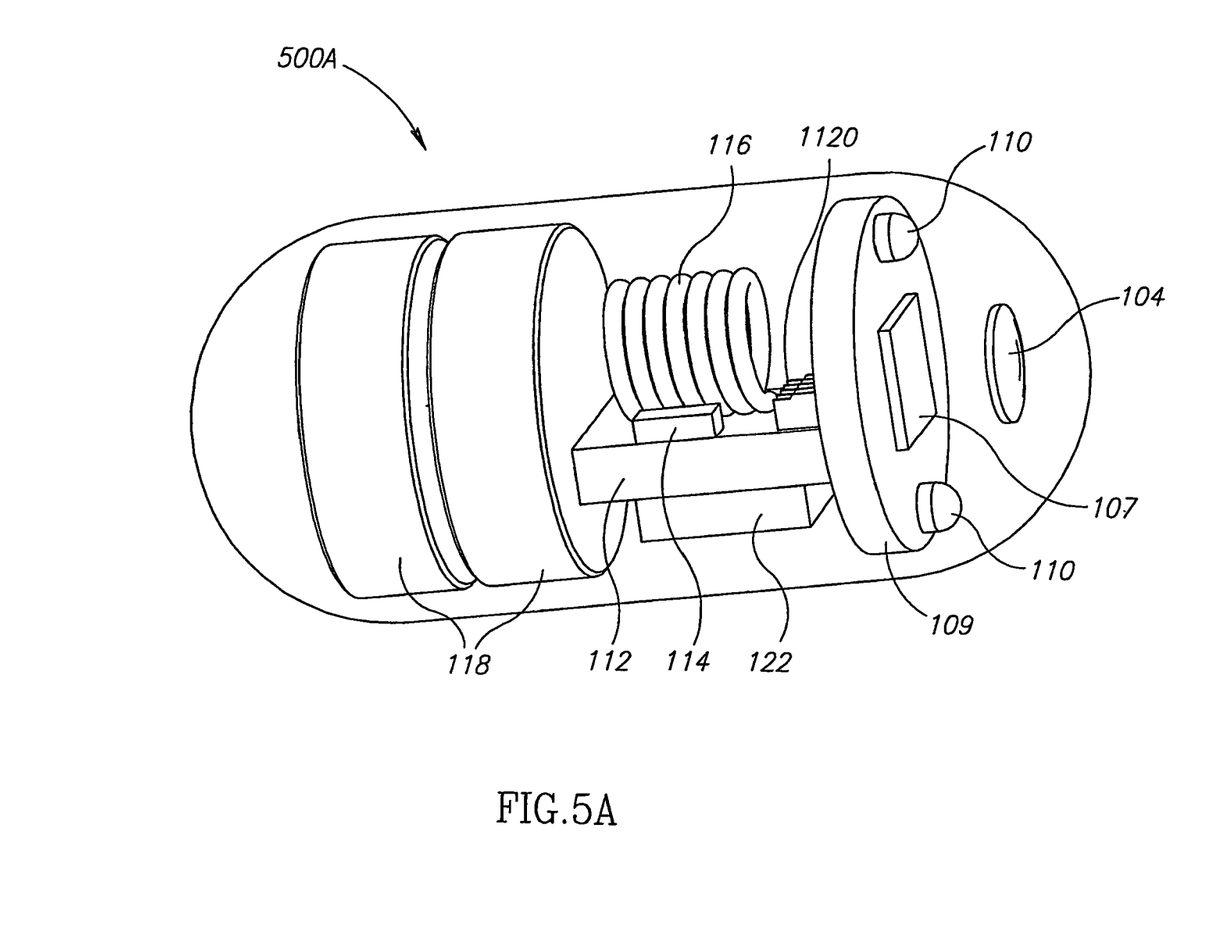
FIGS. 5A-5C are schematic illustrations of different possible arrangements of an antenna within an imaging device according to embodiments of the invention.
Figure 5B:
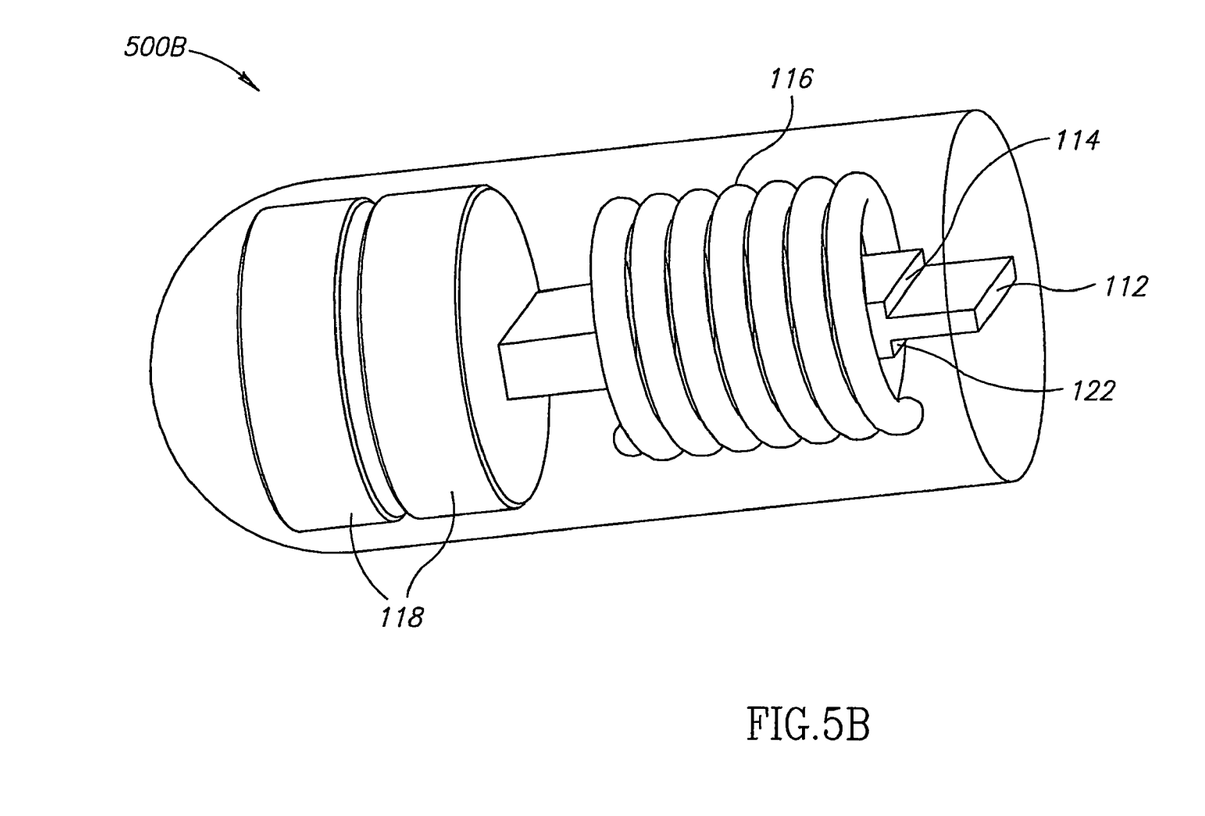
Figure 5C:
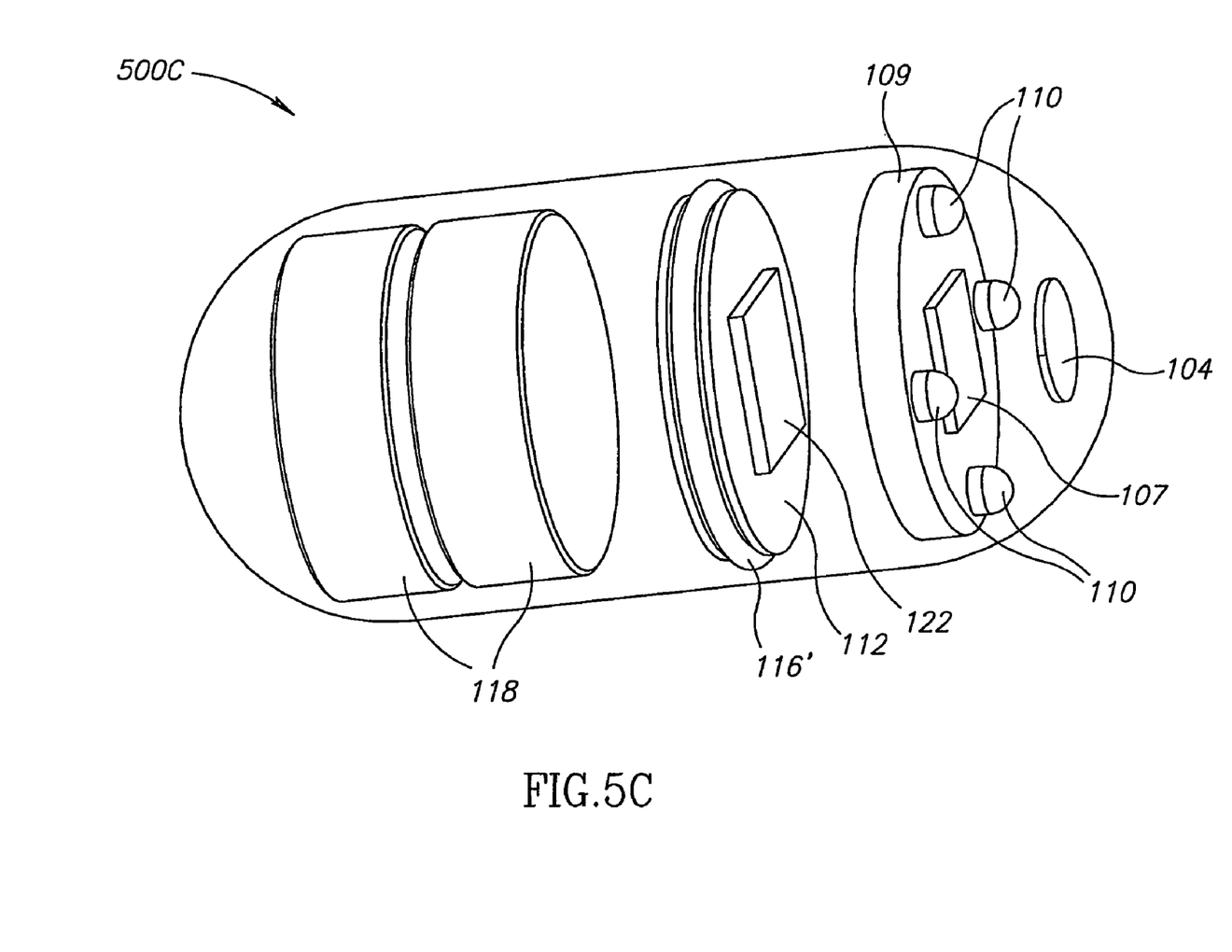

Reference is now made to FIGS. 5A-5C, which are schematic illustrations of different possible arrangements of components in an in vivo imaging device, according to embodiments of the invention. Similar numerals to those in the figures described above have been assigned to like elements. In FIG. 5A components in an imaging device 500A, such as the transmitter 122, processing device or chip 114 and additional components 1120 such as resistors, capacitors, switches etc., are arranged on circuit board 112. Circuit board 112, which may extend from the imaging sensor circuit board 109 substantially perpendicularly, may be situated off center relative to imaging sensor circuit board 109, for example, making room for antenna 116 to compactly fit into the imaging device 500A. The antenna 116 may, for example, be disposed substantially between a power source (such as, for example, one or more batteries 118, a device receiving power from an external source, etc.) and the imaging sensor circuit board 109 and/or imager 107. In some imaging or sensing capsules an antenna is positioned along the width of the capsule at one end of the capsule. An arrangement in which the antenna 116 is positioned in between the imaging sensor circuit board 109 and the batteries 118 along the length of the capsule, for example as illustrated in FIG. 5A, may, for example allow the reduction in the length of the device, such as a capsule shaped imaging device. Other or different benefits are possible. Other arrangements of components may be used. Other types and numbers of antennas, with other shapes, may be used.

Another possible arrangement according to an embodiment of the invention is schematically illustrated in FIG. 5B. Device 500B, which may be, for example, oblong or capsule shaped, includes a transmitter 122 and a processing chip 114 arranged on circuit board 112. For clarity, only one end of the device is shown in FIG. 5B. One or more batteries 118 (or other suitable power sources), which are electrically connected to circuit board 112, provide power to the device elements. Antenna 116 may be arranged around the inner diameter of the device 500B substantially surrounding the circuit board 112 and/or the transmitter 122. In such a case, the length of the device 500B may be reduced; other or alternate benefits are possible. Device 500B may be an image sensing device or another sensing device. Sensors, such as a pH sensor, a pressure sensor, an electrical field sensor, an ultrasonic sensor, a temperature sensor or any other known in vivo sensor, may be included in the device, according to embodiments of the invention. Other types and numbers of antennas, with other shapes, may be used.

In FIG. 5C a device 500C is illustrated in which an antenna 116' is substantially embedded into a circuit board 112. Circuit board 112 may be arranged in parallel or in other relations to the image sensor circuit board 109. The embedding of the antenna 116' in the circuit board 112 according to embodiments of the invention may enables using the space previously occupied by the antenna, for example for adding additional components to the device. Alternatively the unused space may be eliminated from the device 500C thereby reducing the device overall dimensions. Other types and numbers of antennas, with other shapes, may be used. Other components as described herein, such as lenses 104, imaging sensor 107, etc., may be included.

While the present invention has been described with reference to a few specific embodiments, the description in intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

It will be appreciated by persons skilled in the art that the present invention is not limited by what has been particularly shown and described herein above. Rather the scope of the invention is defined by the claims, which follow.

The invention claimed is:

1. An in vivo imaging device comprising:
 a first rigid circuit board having disposed thereon an image sensor, said first circuit board having a top surface and a bottom surface; and
 a second rigid circuit board comprising a cut out sized for accommodating at least one power source, said second circuit board being in electrical communication with the first circuit board and extending at an angle of about 90° from the bottom surface of the first circuit board, said second circuit board having disposed thereon at least one illumination source illuminating in a direction substantially perpendicular to said second circuit board.

2. The device according to claim 1 wherein the illumination source includes an LED.

3. The device according to claim 1 wherein the second circuit board comprises circuitry for processing image signals.

4. The device according to claim 1 wherein the second circuit board is configured for accommodating an ASIC.

5. The device according to claim 1 wherein the second circuit board is configured for accommodating a transmitter.

6. The device according to claim 1 comprising a light redirecting device.

7. The device according to claim 6 wherein the light redirecting device is selected from the group consisting of: a prism, a mirror and a fiber optic light guide.

8. The imaging device according to claim 6, wherein light redirected by said light redirecting device is redirected in a direction parallel to said second circuit board.

9. In an in vivo imaging device, a first rigid circuit board having disposed thereon an image sensor, said first circuit board configured for being in electrical communication with a second rigid circuit board and extending substantially perpendicularly to the second circuit board, wherein said second rigid circuit board comprises a cut out sized for accommodating at least one power source and has disposed thereon at least one illumination source illuminating in a direction substantially perpendicular to said second circuit board.

10. The imaging device according to claim 9, wherein said first circuit board comprises attaching means for attaching the first circuit board substantially perpendicularly to the second circuit board.

11. The imaging device according to claim 10 wherein the attaching means includes electrically communicating means.

12. The imaging device according to claim 9 comprising circuitry for processing image signals.

13. The imaging device according to claim 9 wherein the imaging device is configured for accommodating at least a transmitter.

14. The imaging device according to claim 9 wherein the imaging device is configured for accommodating at least an illumination source.

15. The imaging device according to claim 14 wherein the illumination source includes an LED.

16. The imaging device according to claim 9, further comprising a light guide for altering the path of light emitted from said illumination source.

17. The imaging device according to claim 16, wherein said path of light emitted is altered in a direction parallel to said second circuit board.

18. In an in vivo imaging device, an image sensor, said sensor configured for being in electrical communication with a rigid circuit board, said circuit board extending substantially perpendicularly to the image sensor, wherein said circuit board comprises a cut out sized for accommodating at least one power source and has disposed thereon at least one illumination source illuminating in a direction substantially perpendicular to said circuit board.

19. The imaging device according to claim 18 wherein the sensor comprises a second circuit board having a socket or slot configured for accommodating a side edge of said first circuit board.

20. The imaging device according to claim 19 wherein the socket or slot comprises communication means for electrically communicating with the second circuit board.

21. The imaging device according to claim 18, further comprising a light guide for altering the path of light emitted from said illumination source.

22. The imaging device according to claim 21, wherein said path of light emitted is altered in a direction parallel to said circuit board.

23. A capsule comprising:
 an optical window behind which are disposed:
 an illumination source;
 a first rigid circuit board configured for accommodating at least an image sensor, said first circuit board having a bottom surface; and
 a second rigid circuit board comprising a cut out sized to accommodate at least one power source, said second circuit board being in electrical communication with the first circuit board and extending substantially perpendicularly from the bottom surface of the first circuit board, wherein said illumination source is disposed on said second circuit board and illuminates in a direction substantially perpendicular to said second circuit board.

24. The capsule according to claim 23, further comprising a light guide for altering the path of light emitted from said illumination source.

25. The capsule according to claim 24, wherein said path of light emitted is altered in a direction parallel to said second circuit board.

* * * * *

UNITED STATES PATENT AND TRADEMARK OFFICE
CERTIFICATE OF CORRECTION

| | | |
|---|---|---|
| PATENT NO. | : 7,662,093 B2 | Page 1 of 1 |
| APPLICATION NO. | : 10/529736 | |
| DATED | : February 16, 2010 | |
| INVENTOR(S) | : Gilad et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this

Twenty-eighth Day of December, 2010

David J. Kappos
*Director of the United States Patent and Trademark Office*